(12) United States Patent
Geffen et al.

(10) Patent No.: US 9,335,283 B2
(45) Date of Patent: May 10, 2016

(54) METHOD AND A SYSTEM FOR RECOGNIZING VOIDS IN A BUMP

(75) Inventors: Micha Geffen, Misgav (IL); Doron Reinis, Givat Ela (IL)

(73) Assignee: XWINSYS LTD. (IL)

( * ) Notice: Subject to any disclaimer, the term of this patent is extended or adjusted under 35 U.S.C. 154(b) by 218 days.

(21) Appl. No.: 14/234,169

(22) PCT Filed: Sep. 2, 2012

(86) PCT No.: PCT/IL2012/050342
§ 371 (c)(1),
(2), (4) Date: Jan. 22, 2014

(87) PCT Pub. No.: WO2013/038406
PCT Pub. Date: Mar. 21, 2013

(65) Prior Publication Data
US 2014/0161224 A1    Jun. 12, 2014

Related U.S. Application Data

(60) Provisional application No. 61/573,698, filed on Sep. 12, 2011.

(51) Int. Cl.
*G01N 23/223* (2006.01)
*G01N 23/22* (2006.01)
*G01N 23/225* (2006.01)
*G01R 31/26* (2014.01)

(52) U.S. Cl.
CPC ............ *G01N 23/22* (2013.01); *G01N 23/2252* (2013.01); *G01R 31/26* (2013.01); *G01N 2223/6113* (2013.01)

(58) Field of Classification Search
None
See application file for complete search history.

(56) References Cited

U.S. PATENT DOCUMENTS

| 5,097,492 | A | * | 3/1992 | Baker | G01N 23/043 378/205 |
| 5,621,811 | A | * | 4/1997 | Roder | G01N 23/043 348/126 |
| 6,564,987 | B2 | * | 5/2003 | Imai | B23K 3/0623 228/102 |
| 6,697,454 | B1 | * | 2/2004 | Nicolich | G21K 1/06 378/48 |
| 7,653,174 | B2 | * | 1/2010 | Mazor | G01N 23/223 378/50 |
| 2006/0054811 | A1 | * | 3/2006 | Shemesh | G01N 23/2252 250/307 |

(Continued)

FOREIGN PATENT DOCUMENTS

| WO | WO 2006/010091 | | 1/2006 | | |
| WO | WO 2006010091 | A2 * | 1/2006 | ......... | G01N 23/2252 |
| WO | WO 2006010091 | A3 * | 7/2006 | ......... | G01N 23/2252 |

*Primary Examiner* — Andrew Smyth
(74) *Attorney, Agent, or Firm* — Law Offices of Steven W. Weinrieb

(57) ABSTRACT

A method and a system for bump's inspection are disclosed. The inspection done by comparing the volume of the bump's outside contour and the volume the solid materials from which the bump is made and/or analyzing the bump's solid materials ratio. Principally, the inspection id done by preparing an empiric reference table of the emitted energy received from the solid materials, from which a reference proper bump with a given volume is comprised, using ED-XRF (Energy-Dispersive-X-ray-Fluorescence analysis) analyze; obtaining a first calculated volume of the bump, using a 3D image-processing method; adapting the reference table according to the difference between the given volume and the first calculated volume of the bump; performing a second volume calculation of the bump by applying ED-XRF technology. The difference between the first and second volume calculations and the solid material combination are used to inspect the bump.

10 Claims, 4 Drawing Sheets

(56) References Cited

U.S. PATENT DOCUMENTS

| | | | |
|---|---|---|---|
| 2010/0021050 A1* | 1/2010 | Kakuda | B23K 1/0016 382/150 |
| 2010/0165094 A1* | 7/2010 | Kakuda | G01B 11/24 348/92 |
| 2011/0123098 A1* | 5/2011 | Ernst | G01B 11/2513 382/154 |

* cited by examiner

METHOD AND A SYSTEM FOR RECOGNIZING VOIDS IN A BUMP

FIELD OF INVENTION AND BACKGROUND

The present invention relates to the field of wafers inspection, more specifically the present invention relates to a method and a system for inspecting the existence of voids in a bump and calculating the voids' volume.

A "bump" is a half sphere shaped salient, made of solderable material, located on the face of a microelectronic chip. The bump exists in some chips and substitutes as leads by means of which the component is connected to the printed circuit when the bumps are soldered to the board. The bump shape is a half ball alike and a chip can contain a large number of bumps. During the last few years the electronics industry moved from SnPb solders to Lead-free solders. Today the high lead SnPb bumps are exempted from the WEEE and RoHS directives. In the new wafers technologies a use of SnAg can be found instead of SnPB.

The typical bumps' dimensions are 50-60 μm in diameter and 20-30 μm in height. The skullcap is placed on a 50-60 μm diameter pillar of Copper with a height of approximately 50 μm. The whole structure is placed on a Silicon base with a top layer of passivation made of polymer.

During the wafer's production voids can be created in the soldering layer of the bump and in case that the volume of the voids passes a threshold the quality of the product is damaged. Usually, a threshold of 0.01% of volume is used in the wafer's quality inspection.

The present invention uses two well stable technologies to recognize void or voids in a bump and estimates the total volume of the voids inside the bump.

There are several technologies for calculating the volume of an object using 3D imaging process, one of these technologies is the first that is used in the present invention.

The second technology known as ED-XRF (Energy-Dispersive-X-ray-Fluorescence analysis) this technology is a well-established and stable technology used for years in the industry. In the last two years there was a great advance in this technology with the adoption of SD Detectors that enable much better resolution and count rate. This gives the ability to go down to lower levels of detection limits in much less time. This technology is a spectroscopy method belongs to the high energy spectroscopy process. The technology utilizes an emission of the characteristic lines. While an atom is hit by X-ray a characteristic energy is emitted from the atom and this energy is analyzed into the materials spectra of qualification and quantification. In a provided diagram, each of the bump's soldering material is presented as a column, the magnitude of the column represent the material volume.

X-ray optics can be used to enhance ED=XRF instrumentation. For conventional XRF instrumentation, typical focal spot sizes at the sample surface range in diameter from several hundred micrometers up to several millimeters. Polycapillary focusing optics collects X-rays from the divergent X-ray source and direct them to a small focused beam at the sample surface with diameters as small as tens of micrometers. The resulting increased intensity delivered to the sample in a small focal spot allows for enhanced spatial resolution for small feature analysis and enhanced performance for measurement of trace elements for Micro EDXRF applications.

The present invention combines these technologies and provides a method and a system for inspecting bumps.

SUMMARY OF THE INVENTION

The present invention is a method and a system for bump's inspection by comparing the volume of the bump's outside contour and the volume the solid materials from which the bump is made and/or analyzing the bump's solid materials ratio.

According to a preferred embodiment of the present invention it is provided a method for bump's inspection by comparing the volume of the bump's outside contour and the volume the solid materials from which the bump is made and/or analyzing the bump's solid materials ratio. The outside contour volume is calculated by using three dimensional image processing.

According to another preferred embodiment the method is provided, wherein the solid material volume is calculated by ED-XRF (Energy-Dispersive-X-ray-Fluorescence analysis) analyze.

According to another preferred embodiment the method is provided, wherein the method is used for recognizing void or voids in a bump and calculating the volume of the void of voids, if void or voids are exist in the bump and this method is comprised of the following steps: preparing an empiric reference table of the emitted energy received from the solid materials, from which a reference proper bump with a given volume is comprised, using ED-XRF (Energy-Dispersive-X-ray-Fluorescence analysis) analyze; obtaining a first calculated volume of the bump, using a 3D image-processing method; adapting the reference table according to the difference between the given volume and the first calculated volume of the bump; performing a second volume calculation of the bump by applying ED-XRF technology.

The recognition of void or voids in the bump and the calculation of the void or voids volume is done by applying the following functions: if the first calculated volume and the second calculated volume are equal, the bump does not contains voids; if there is a difference between the first calculated volume and the second calculated volume, the difference represent the volume of void or voids in the bump; and if the volume of void or voids volume is large than a predetermined threshold, the bump should be disqualified.

According to another preferred embodiment the method used polycapillary focusing optics to collect the X-rays from the tube into a small focused narrow beam.

According to another preferred embodiment the method is provided, wherein the method is used for analyzing the bump's solid materials ratio in order to inspect whether the bump's material combination matches the combination criteria.

According to another aspect of the present invention it is provided a system for bump's inspection, and this system is comprised of: an optical means for aiming the system to the inspected bump and capturing 3D image of the inspected bump; an X-ray tube to project X-ray on the inspected bump; an X-ray detector for detecting fluoresces radiation that is reflected from the inspected bum while projecting; and a computing system.

The computing system is operative for: storing an empiric reference table of the emitted energy received from the solid materials, from a reference proper bump with a given volume, obtained from ED-XRF analyze; using the optical means to provide information to aim the system to the inspected bump to a spot position of the X-ray tube and X-ray detector; calculating the outside contour volume of the inspected bump, using the captured 3D image; adapting the reference table according to the volume difference between the reference proper bump and the outside contour volume; using the reflected fluoresces radiation and ED-XRF analyze to obtain the volume of each solid materials, from which the inspected bump is made; comparing the total volume of the solid materials with the calculated outside contour volume of the inspected bump; and reporting: the volume of each solid material contains in the inspected bump; the total volume of all solid materials of the inspected bump; the calculated volume of the outside contour of the inspected bump; and the result of the volume comparison.

According to another preferred embodiment the provided system further includes a polycapillary focusing optics in order to collect the X-rays from the X-ray tube into a small focused narrow beam.

According to another preferred embodiment the system is provided wherein the geometry position of the X-ray tube, the X-ray detector and the optical means is fix geometry.

According to another preferred embodiment the system is provided wherein the spot size of said X-ray tube is in the range og 1-0100 μm.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the figure.

DESCRIPTION OF THE PREFERRED EMBODIMENTS

The present invention is a method and a system for bump's inspection by comparing the volume of the bump's outside contour and the volume the solid materials from which the bump is made and/or analyzing the bump's solid materials ratio.

The principles and operation of the method and system according to the present invention may be better understood with reference to the figure and the accompanying description.

Figure 1:
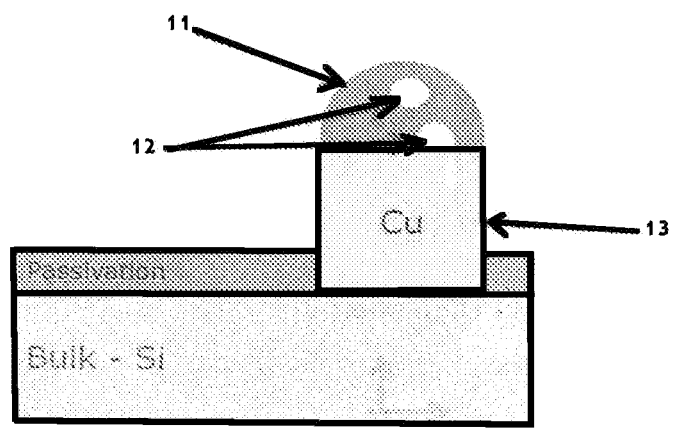
FIG. 1 illustrates a bump for inspection.

FIG. 1 illustrates a bump for inspection. The bump 11 is located on copper 13 and one of the typical defects that should be inspected is a missing material that creates void or voids 12 inside the bump 11. If the total volume of the voids 12 is larger from a given threshold, the bump is indicated as defective bump.

Figure 2:
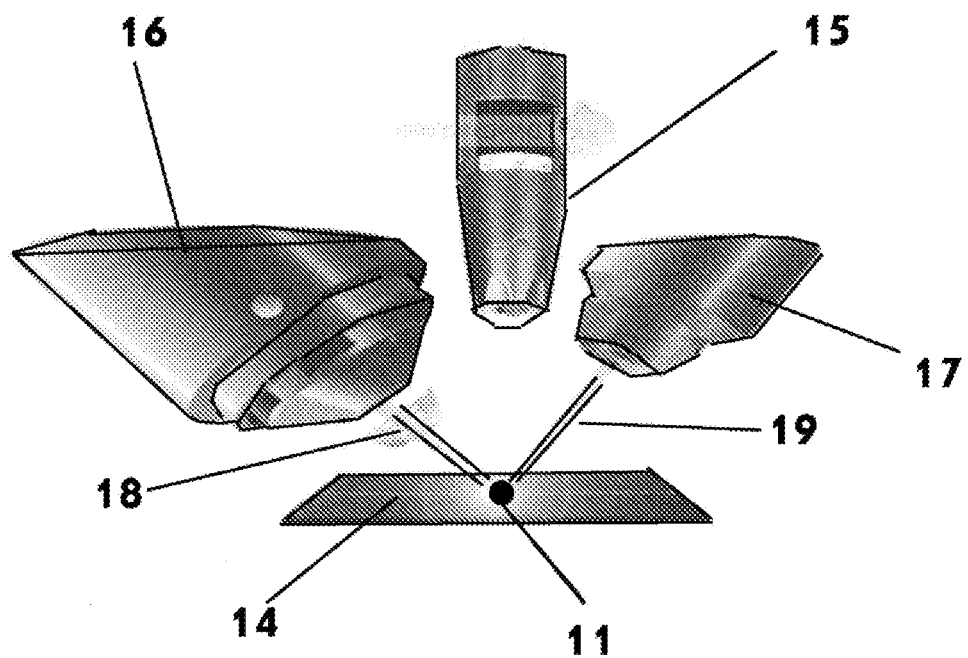
FIG. 2 illustrates a setup of the system according to the present invention.

FIG. 2 illustrates a setup of the system according to the present invention. The inspected bump 11 is located on the wafer 14. The system uses the optical means 15 to navigate the setup—including the X-ray tube 16 and the X-ray detector 17—to the right spot position. The optical means 15 captures a 3D bump's image and the computing system (not shown) calculate the bump's 11 volume according the outline of its contour. X-ray are projected from the X-ray tube 16 on the inspected bump 11 and a fluorescence energy is emitted from the bump's 11 material and is detected by the X-ray detector 17.

Figure 3:
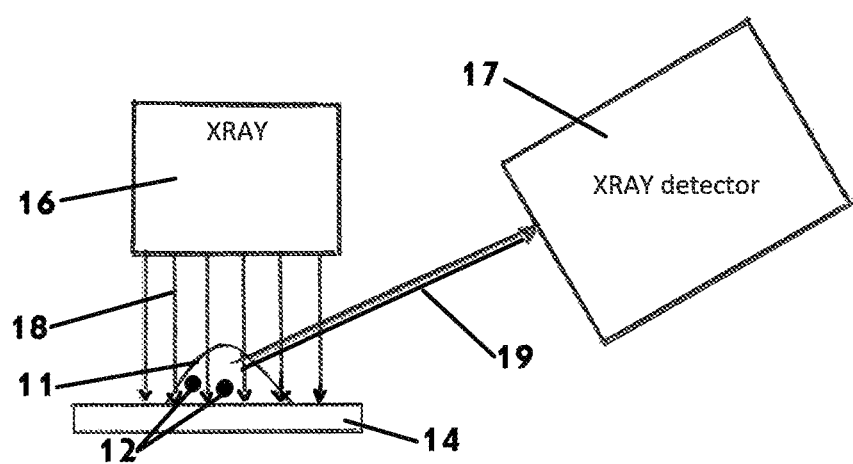
FIG. 3 illustrates ED-XRF's setup.
Figure 4:
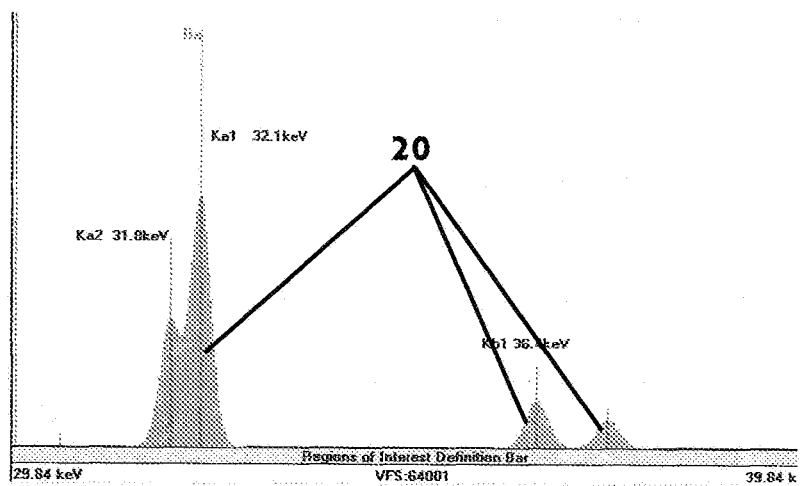
FIG. 4 illustrates results of ED-XRF analyze.

FIG. 3 illustrates ED-XRF's setup. In order to analyze the solid materials that are combined the bump 11 using ED-XRF technology, the X-ray tube 16 projects high X-ray energy 18 on the inspected bump 11. Fluorescence energy 19 is emitted from the solid material of the bump 11 and detected by the X-ray detector 17. From the detected energy, the volume of each solid material of the bump 11 can be obtained—as illustrated in FIG. 4. In the illustrated case there is a void 12 in the bump. Therefore, the sum of the materials' volumes that are combined the bump 11 is less than the bump's volume that was calculated by using the imaging process of the 3D image. The volumes difference represents the void's volume.

FIG. 4 illustrates results of ED-XRF analyze. The ED-XRF technology analyzes the solid materials from which the fluorescence energy was emitted. Energy Transitions will result in emitted photons and is measured. A spectra graph that represents qualification and quantification analysis is presented. Each of the soldering material is illustrated by a column 20 and the magnitude of the column represents the material volume. The sum of the volumes is the solid materials of the bump.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

What is claimed is:

1. A method for the detection of the presence of a void within a bump comprising solid materials and having a particular outside contour, and for the determination of the volume of said void within said bump, comprising the steps of:
   determining the volume of said outside contour of said bump;
   determining the volume of said solid materials from which said bump is made; and
   comparing the volume of said solid materials comprising said bump with said volume of said outside contour of said bump,
   whereby if said volume of said solid materials comprising said bump is less than said volume of said outside contour of said bump, then at least one void exists within said bump and the volume of said at least one void located within said bump comprises the difference between said volume of said outside contour of said bump and said volume of said solid materials comprising said bump.

2. The method of claim 1, wherein said outside contour volume is calculated by using three dimensional image processing.

3. The method of claim 1, wherein said solid material volume is calculated by ED-XRF (Energy-Dispersive X-Ray Fluorescence) analysis.

4. The method of claim 3, wherein said method is used for analyzing said bump's solid material ratio in order to inspect whether said bump's material combination matches combination criteria.

5. The method of claim 1, wherein said method is used for recognizing a void or voids in a bump and calculating the volume of said void or voids, if said void or voids exist in said bump, said method further comprising the steps of:
   preparing an empirical reference table of the emitted energy received from the solid materials, from which a reference bump with a predetermined volume is comprised, using ED-XRF (Energy-Dispersive X-Ray Fluorescence) analysis;

obtaining a first calculated volume of said bump, using a 3D image-processing method;

adapting said reference table according to the difference between said predetermined volume and said first calculated volume of said bump;

performing a second volume calculation of said bump by applying ED-XRF technology; and recognizing the existence of a void or voids in said bump and calculating the volume of said void or voids by applying the following functions:

if said first calculated volume and said second calculated volume are equal, said bump does not contain voids;

if there is a difference between said first calculated volume and said second calculated volume, said difference represents the volume of the void or voids in said bump; and if said volume of the void or voids is larger than a predetermined threshold, said bump should be disqualified.

6. The method of claim 5, wherein said method further uses polycapillary focusing optics to collect X-rays from an X-ray tube, dgsfhAused in said ED-XRF (Energy-Dispersive X-Ray Fluorescence) analysis, in a small focused narrow beam.

7. A system for the inspection of a bump, comprising:

an optical means for aiming the system toward a bump to be inspected and for capturing a 3D image of said inspected bump;

an X-ray tube for projecting X-rays onto said inspected bump;

an X-ray detector for detecting fluorescent radiation that is reflected from said inspected bump; and a computing system comprising:

means for storing an empirical reference table of the emitted energy received from the solid materials, from a reference proper bump with a given volume, obtained from ED-XRF analysis;

means for using said optical means to provide information to aim said inspected bump to a spot position of said X-ray tube of said X-ray detector;

means for calculating the outside contour volume of said inspected bump, using said captured 3D image;

means for adapting said reference table according to the volume difference between said reference proper bump and said outside contour volume;

means for using said reflected fluorescent radiation and said Ed-XRF analysis so as to obtain the volume of each one of said solid materials, from which said inspected bump is made;

means for comparing the total volume of said solid materials with the calculated outside contour volume of said inspected bump; and means for reporting the volume of each one of said solid materials contained in said inspected bump; the total volume of all solid materials of said inspected bump; the calculated volume of the outside contour of said inspected bump; and the result of said volume comparison.

8. The system of claim 7, further comprising includes a polycapillary focusing optics in order to collect said X-rays from said X-ray tube into a small focused narrow beam.

9. The system of claim 7 wherein the geometry position of said X-ray tube, said X-ray detector, and said optical means is fixed geometry.

10. The system of claim 7 wherein the spot size of said X-ray tube is in the range of 1-0100 μm.

* * * * *